United States Patent
Gilad et al.

(10) Patent No.: US 7,625,338 B2
(45) Date of Patent: Dec. 1, 2009

(54) IN-VIVO SENSING DEVICE WITH ALTERABLE FIELDS OF VIEW

(75) Inventors: Zvika Gilad, Haifa (IL); Alex Blijevsky, Yoqneam Illit (IL)

(73) Assignee: Given Imaging, Ltd., Yoqneam (IL)

( * ) Notice: Subject to any disclaimer, the term of this patent is extended or adjusted under 35 U.S.C. 154(b) by 673 days.

(21) Appl. No.: 11/023,524

(22) Filed: Dec. 29, 2004

(65) Prior Publication Data

US 2005/0143644 A1    Jun. 30, 2005

Related U.S. Application Data

(60) Provisional application No. 60/533,244, filed on Dec. 31, 2003.

(51) Int. Cl.
  A61B 1/05    (2006.01)
  A61B 1/04    (2006.01)
  A61B 1/06    (2006.01)

(52) U.S. Cl. .................... 600/173; 600/160

(58) Field of Classification Search ............ 600/160, 600/173, 175, 114, 407, 476
See application file for complete search history.

(56) References Cited

U.S. PATENT DOCUMENTS

| | | | | |
|---|---|---|---|---|
| 3,532,037 A | * | 10/1970 | Auphan et al. ............ 359/211 |
| 3,773,039 A | * | 11/1973 | Mori et al. ................ 600/173 |
| 4,278,077 A | | 7/1981 | Mizumoto | |
| 4,919,114 A | * | 4/1990 | Miyazaki .................. 600/110 |
| 5,489,256 A | * | 2/1996 | Adair ....................... 600/133 |
| 5,604,531 A | | 2/1997 | Iddan et al. | |
| 5,827,176 A | * | 10/1998 | Tanaka et al. ............. 600/109 |
| 5,993,378 A | | 11/1999 | Lemelson | |
| 6,240,312 B1 | | 5/2001 | Alfano et al. | |
| 6,371,909 B1 | * | 4/2002 | Hoeg et al. ............... 600/173 |
| 6,428,470 B1 | * | 8/2002 | Thompson ................ 600/173 |
| 6,537,210 B1 | * | 3/2003 | Wulfsberg ................ 600/173 |
| 2002/0022767 A1 | * | 2/2002 | Dohi et al. ................ 600/173 |
| 2002/0103417 A1 | | 8/2002 | Gazdzinski | |
| 2003/0032863 A1 | * | 2/2003 | Kazakevich .............. 600/173 |
| 2003/0073935 A1 | | 4/2003 | Segawa et al. | |
| 2003/0130562 A1 | * | 7/2003 | Barbato et al. ............ 600/109 |
| 2003/0171652 A1 | | 9/2003 | Yokoi et al. | |
| 2003/0181788 A1 | | 9/2003 | Yokoi et al. | |
| 2003/0229268 A1 | | 12/2003 | Uchiyama et al. | |
| 2004/0111011 A1 | | 6/2004 | Uchiyama et al. | |
| 2005/0119577 A1 | * | 6/2005 | Taniguchi ................ 600/459 |

(Continued)

FOREIGN PATENT DOCUMENTS

WO    WO 01/65995    9/2001

(Continued)

*Primary Examiner*—John P Leubecker
(74) *Attorney, Agent, or Firm*—Pearl Cohen Zedek Latzer, LLP

(57) ABSTRACT

A device and system for in-vivo imaging with changeable fields of view includes a capsule shaped housing having an external shell that is adapted to be swallowed and passed through a patient due to the housing having no physical connection to the outside. The housing encloses an imaging unit that includes an imager and an illumination source, and a rotatable structure to alter the field of view of the imaging unit. The rotatable structure includes a motor that rotates the imaging unit relative to the and within the external shell. External commands transmitted from outside a patient can control the rotatable structure.

21 Claims, 3 Drawing Sheets

U.S. PATENT DOCUMENTS

| | | | |
|---|---|---|---|
| 2005/0154277 A1* | 7/2005 | Tang et al. | 600/407 |
| 2006/0004255 A1* | 1/2006 | Iddan et al. | 600/160 |
| 2006/0004276 A1* | 1/2006 | Iddan et al. | 600/407 |
| 2006/0052708 A1* | 3/2006 | Iddan et al. | 600/476 |
| 2007/0032700 A1* | 2/2007 | Fowler et al. | 600/173 |
| 2007/0142710 A1* | 6/2007 | Yokoi et al. | 600/173 |
| 2007/0161862 A1* | 7/2007 | Yokoi et al. | 600/175 |

FOREIGN PATENT DOCUMENTS

| | | |
|---|---|---|
| WO | WO 2004/028336 | 4/2004 |

* cited by examiner

IN-VIVO SENSING DEVICE WITH ALTERABLE FIELDS OF VIEW

RELATED APPLICATION DATA

This application claims benefit from U.S. provisional application Ser. No. 60/533,244, filed on Dec. 31, 2003 entitled ROTATING IN-VIVO SENSING DEVICE, which is incorporated in its entirety by reference herein.

FIELD OF THE INVENTION

The present invention relates to the field of in-vivo sensing. More specifically the present invention relates to an in-vivo sensing device with alterable spatial fields of view.

BACKGROUND OF THE INVENTION

Devices for performing in-vivo sensing, such as imaging, of body passages or cavities, are known in the art. Such devices may include, inter alia, various endoscopic imaging systems and autonomous devices for performing imaging in various internal body cavities. Other sensing devices, such as pH or temperature sensing devices, are known.

An autonomous in-vivo imaging device may include, for example, an imager for obtaining images from inside a body cavity or lumen, such as the gastrointestinal (GI) tract. The imager may, for example, be associated with an optical system, and optionally a transmitter and an antenna. Other types of in-vivo sensing devices may exist, such as endoscopes which may not require a transmitter and/or antenna, and devices performing functions other than imaging.

Typically, the field of view of an autonomous in vivo imaging device may be defined by optical components of the device, such as any lenses or viewing window the device may have, and by the orientation the device may assume while propagating through the intestine.

SUMMARY OF THE INVENTION

Various embodiment of the present invention may provide an in-vivo sensing device that may alter its field of view. In some embodiments of the present invention, the sensing device may include a sensor to sense in-vivo conditions in a body and rotating capability to rotate a structure within said sensing device so as to alter the field covered by the sensor.

In one embodiment of the present invention, the sensing device may be an in-vivo imaging device and the rotating means may be a motor with a shaft. According to an embodiment of the invention the rotating means may rotate an imaging unit relative to an external shell of the in-vivo device. In another embodiment of the present invention, the rotating means may rotate a reflective element that may reflect light toward an imager within the in-vivo device. In other embodiments, other structures within an in-vivo device may be rotated, for example an imager, optical system, mirror, prism, shell, window, etc., or other structures.

According to embodiments of the present invention the in-vivo sensing device may transmit image data and/or other data to an external receiver. Transmitted data may, for example, be stored, processed and/or displayed. According to an embodiment of the present invention, an external transmitter may transmit commands to the in-vivo device to, for example, alter its field of view or alter one or more operational modes of the in-vivo device.

BRIEF DESCRIPTION OF THE DRAWINGS

The subject matter regarded as the invention is particularly pointed out and distinctly claimed in the detailed description in the specification. The invention, however, may best be understood by reference to the following detailed description when read with the accompanied drawings in which:

Figure 1:
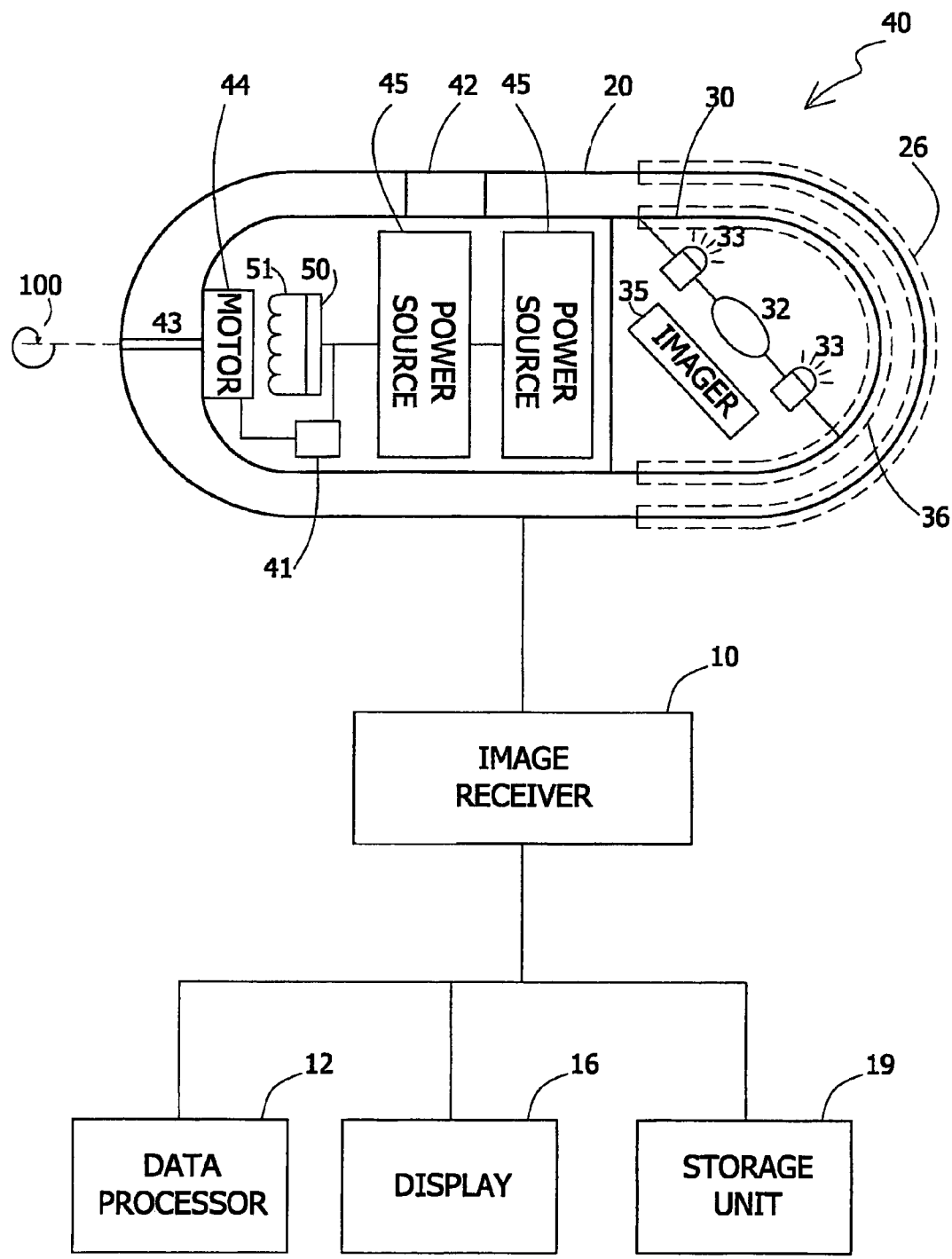
FIG. 1 is a schematic illustration of an in-vivo sensing device according to an embodiment of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate, corresponding or analogous elements.

DETAILED DESCRIPTION OF THE INVENTION

In the following description, various aspects of the invention are set forth. For purposes of explanation and in order to provide an understanding of the invention, specific configurations and details are set forth in order to provide a thorough understanding of the present invention. However, it will also be apparent to one skilled in the art that the invention may be practiced without the specific details presented herein. Furthermore, well-known features may be omitted or simplified in order not to obscure the invention.

A device according to some embodiments of the present invention may provide for, for example, a changeable field, a wide-field, a circular field, and/or other fields of sensing, such as fields of view. For example, in one embodiment, one or more structures and/or elements within an in-vivo device may rotate, for example, with respect to another structure and/or element of the in-vivo device. In one embodiment of the present invention, an imaging unit, for example, an imaging unit within an in-vivo device may rotate with respect to an external and/or outer shell, housing, and/or container of the in-vivo device. The device may include, for example, an actuator, e.g. a motor, or other rotating means for rotating one or more structures within the in-vivo device. In one embodiment of the present invention, a gear, correction device, dampening system, etc., may be used to stabilize and/or tailor the motion imparted by the actuator. In another embodiment of the present invention, an external magnetic field obtained from a magnetic field generator may be used to rotate the imaging unit with respect to the external shell. Typically, the magnetic field generator may generate a rotating magnetic field. In other embodiments, other suitable magnetic fields may be generated. In such an example, the strength of the magnetic field may be small compared to the strength of the magnetic field required to rotate the external shell (that may be held within a body lumen) due to the low friction coefficient of, for example the axis of rotation. In such an embodiment a magnet, e.g. a permanent magnet may be included in the imaging unit and an external magnetic field may cause the permanent magnet and any structure fixed to the magnetic field to rotate about, for example, an axis of rotation. Other suitable methods of rotating an imaging unit may be used. In other embodiments other suitable elements may be used to rotate or otherwise move one or more structures and/or elements of the in-vivo device and the structure and/or element may be made to rotate or be displaced in different manners using other suitable means.

Referring to FIG. 1, device 40 may be an in-vivo sensing device. It is noted that some embodiments of the present invention may be directed to, for example, a typically swallowable, autonomous in-vivo device. Other embodiments need not be swallowable and/or autonomous. Devices according to embodiments of the present invention may, for example, be similar to embodiments described in International Application WO 01/65995, entitled "A Device and System For In-vivo Imaging", published on Sep. 13, 2001 and/or in U.S. Pat. No. 5,604,531, to Iddan et al, both of which are assigned to the common assignee of the present invention and both are hereby fully incorporated by reference. Furthermore, a receiving and/or display system suitable for use with embodiments of the present invention may also be similar to embodiments described in WO 01/65995 and/or in U.S. Pat. No. 5,604,531. Devices and systems as described herein may have other configurations and other sets of components.

According to some embodiments of the present invention device 40 may typically include an imaging unit 30, within an external housing and/or shell 20. Typically, each of imaging unit 30 and shell 20 may be, for example, capsule shaped, although the present invention may not be restricted to a capsule shape alone and may have other shapes, for example, a tubular, spherical, conical, or other suitable shapes. Typically the shape of each of the imaging unit 30 and the shell 20 may be matched and one may rotate within or with respect to the other. Typically, inner imaging unit 30 may. be smaller than and contained within shell 20.

According to one embodiment of the present invention, device 40 may include an actuator, for example motor 44 with motor shaft 43 for providing rotational capabilities, a gear mechanism 42 for stabilization rotating motion, a controller 41 for controlling the motor or other mechanism for providing rotation, an imager 35, an illumination source 33 and an optical system 32 for capturing images in, for example, the inner cavities and body lumens, a transmitter 50 and an antenna 51 for transmitting a signal, e.g. signals from imager 35, and a power source 45 for providing power to electrical elements of the device 40. According to some embodiments of the present invention, the optical system 32 may include, for example, a mirror, a prism, a lens, any other suitable optical element, and/or any combination of elements thereof In one embodiment of the present invention, one or more elements of the optical system may be rotatable.

Transmitter 50 with antenna 51 may transmit images and other data to a receiver 10. Data transmitted may be displayed, for example on a display 16, processed with processor 12 and stored in, for example, storage unit 19. Receiver 10, display 16, processor 12, and storage unit i9 may be incorporated within one or more units. For example, display 16, processor 12 and storage unit 19 may be, for example, integral to a work station. Receiver 10 may have a separate storage unit to temporarily store received data and may in some embodiments. of the present invention, be a portable device. In other embodiments other configuration may be used and there may be more than one display unit 16 and processor 12, for example, a portable receiver 10 may include a display and processor as well, other configurations may be used. In some embodiments of the present invention, receiver 10 may also have capabilities of transmitting commands to device 40, for example, via user input means. For example, a user may view images on display 16 transmitted on-line from device 40, and may, for example, based on data viewed, send commands to device 40 to, for example, change and/or alter the field of view of imager 35, change the frame rate and/or other operational states. Other suitable methods of control may be implemented. According to some embodiments transmitter 50 may be a transceiver or another receiver may be included in device 40 for receiving signals, e.g., commands from an external source.

Power source 45 may include one or more batteries. For example, power source 45 .may include silver oxide batteries, lithium batteries, other suitable electrochemical cells having a high energy density, or the like. Other suitable power sources may be used. In one embodiment of the present invention, power source 45 may be, for example, a unit capable of accepting power from an external source. Other suitable methods of powering device 40 may be used. According to some embodiments, the device 40 need not have an internal power source but may include a mechanism for receiving power from an external source, e.g., from an external magnetic field.

Imaging unit 30 may typically include components and functionality substantially similar to imaging devices such as those defined in U.S. Pat. No. 5,604,531 or International Application WO 01/65995. However, in other embodiments, other imaging units may be used, and, further, sensing units other than or in addition to imaging units may be used.

Motor 44 may be, for example, a Micro Brushless motor manufactured by Faulhaber, or may be any suitable motor known in the art. In other embodiments, rotational motion may be provided with elements other than and/or in addition to motor 44. For example, electromagnetic mechanisms, gear mechanisms, springs, dampers, etc. may be used together with a motor 44 and/or an actuator other than a motor may be used. In some embodiments of the present invention, the controller 41 may be used to control motion of motor 44. Controller 41 or its functionality may be integral to motor 44, transmitter 50, imager 35, or may be a stand-alone element. Controller 41 may, for example, receive external commands transmitted to device 40, for example, from a user viewing on-line data obtained from device 40, or may receive commands generated within the in-vivo device, for example, from the imager 35, transmitter 50, other sensors and/or components incorporated within device 40, or other suitable elements. In other embodiments of the present invention, the controller 41 may be external to the in vivo device, e.g. controller 41 may be integral to image receiver 10 and/or data processor 12. Commands from controller 41 may, for example, be automatic and/or based on previous .or current data captured by imager 35, or other sensors, for example, pH, temperature, and/or pressure sensor that may be incorporated within device 40. In other embodiments of the present invention, controller 41 may control the capture frame rate and or the transmission of images captured from imager 35. Alternately, the motor or other actuator may rotate at a set rate and/or a set angle without requiring control commands from elements or structures of device 40 and/or processor 12. In one example the motor 44 and/or one or more rotatable structures, e.g. imaging unit 30, may rotate 60 degrees in 200 milliseconds to 5 seconds depending, for example, on the frame capture rate of the imager (e.g. 2 to 14 frames/second). In some embodiments, the controller 41 may be programmed to rotate one or more structures at a fixed rate and/or may be integral to motor 44. In yet other embodiments of the present invention a motor may not be required. For example, an external magnetic field may be used to rotate the imaging unit with respect to the external shell. In such an embodiment a magnet, e.g. a permanent magnet may be included in the imaging unit and an external magnetic field may cause the permanent magnet to rotate. Other suitable methods of achieving rotation with an external magnetic field may be used.

In one embodiment of the present invention, motor 44 may be housed within the imaging unit 30, or in another suitable location and motor shaft 43 may extend through imaging unit 30 and may be, for example, fixed to shell 20. Other suitable configurations for engaging motor 44 with shaft 43 to imaging unit 30 and shell 20 may be used. Suitable connecting or power transfer units, other than a shaft, may be used. Furthermore, other numbers of shafts and/or axles connected to shaft 43 may be used. In one embodiment, motor 44 may rotate imaging unit 30 with respect to shell 20. The rotation may, for example, alter the field of sensing and/or imaging or may provide a broad, alterable, changing and/or wide field of sensing, e.g. a field of imaging and/or a field of view. The rotation rate of the motor 44 may be, for example, constant or variable and may for example be controlled by controller 41 and/or transmitter 50.

In some embodiments of the present invention, the shaft 43 may be stationary and the motor 44 and the structure to which the motor .may be fixed, e.g., imaging unit 30, may rotate. In further embodiments, other configurations or relationships between an imaging unit 30, an outer shell unit 20, and a rotational unit, may cause rotation of a structure or element of the device 40. For example, in some embodiments of the present invention, an axle or other structure connected (possibly via a gear system, such as gear mechanism 42 or another suitable system) to shaft 43 may be used. One or more structures may be rotated with, for example shaft 43. For example, one or more of the imager, one or more elements of the optical system such as a lens, mirror, prism, light guide, aperture, window, a structure holding a set of imaging or optical elements, a shell of an imaging device, etc may be rotated.

Gear mechanism 42 may be any known suitable gear mechanism, for example, a mechanism containing a cam or a set of gears, however it may not be limited to the mechanism mentioned herein and any similar suitable gear mechanism, known in the art may be utilized. In one embodiment, gear mechanism 42 may be positioned in the space between the imaging unit 30 and shell 20 and may rotatably engage imaging unit 30 and outer shell 20 for the purpose of, for example, guiding and stabilizing the rotation. Additional mechanisms, such as bearings, rollers, etc. may be positioned to aid stable rotation. The gear mechanism 42 may, for example, be used to facilitate a smooth motion, to control or regulate the speed of rotation, etc. In an alternate embodiment, a gear or transmission mechanism may be located in other suitable locations. For example, a motor may be connected to a suitable gear or transmission mechanism, which may connect to an axle or other connector to turn a unit within a sensing device. One or more gear(s) 42 may be used. In another embodiment gear 42 may be used to change or alternate the speed of the rotation. In other examples, bearings, rollers, or similar elements may be positioned between shell 20 and imaging unit 30, for example, for providing a substantially frictionless connection between them.

According to one embodiment of the present invention, imager 35 may be positioned on an angle, for example, an angle between 0 and 90 degree with respect to the axis of rotation 100 of motor 44 or to the axis or to the intended movement direction of the device. In another embodiment, the field of sensing of imager 35 (or other sensor) may be at least partially side viewing, e.g. the field of sensing and/or viewing direction may be at an angle, e.g. a 30 to 60 degree angle, with respect to the axis of rotation 100. Imaging components, for example, imager 35 may be angled or otherwise positioned so that when the imaging unit 30 may be rotated the view may change. Rotating imaging unit 30 while capturing image frames, or periodically, between image-frame capture may produce a 360 degree view or alternate views. In other embodiments, a rotating imager 35 or imaging unit 30 may be used to capture a panoramic image. According to some embodiments of the present invention, illumination sources 33 may be rotated together with imager 35. In other embodiments illumination source 33 may not be rotated.

Device 40 may have suitable areas of transparency, e.g. a window area 26 and/or area 36 to allow imaging through imaging unit 30 and shell or container 20. Shell 20 and imaging unit 30 may be partially or entirely transparent, or may have shaped areas of transparency, e.g. area 26 and/or area 36. For example, the shell 20 and imaging unit 30 may include one or more areas and/or portions that may allow the imager 35 an unobstructed external field of view. In alternate embodiments, transparent areas and/or portions may have different shapes. Such shaped areas (e.g. area 26 and/or area 36) may not be limited to one particular shape and may, for example, be a ring shape, semi-spherical or another shape. Outer shell 20, including one or more transparent portions, may be made of, for example, suitable polymer or plastic, e.g., isoplast™.

Imager 35 may include a Complimentary Metal Oxide Semiconductor (CMOS) electronic image sensor including a plurality of elements. In other, embodiments of the invention, imager 35 may include other suitable types of optical sensors and/or devices able to capture images, such as a Charge-Coupled Device (CCD), a light-sensitive integrated circuit, a digital still camera, a digital video camera, or the like. Imager 35 may be an ultra low power image sensor and may be provided in Chip Scale Packaging (CSP). Other types of imagers may be used. In other embodiments, more than one imager 35 may be used. Imager 35, illumination source 33 and optical system 32 may typically be housed within inner imaging unit 30 behind transparent area 36.

Imager 35 may be in electrical communication with transmitter 50. Transmitter 50 may transmit images and/or other data to, for example, image receiver 10, via, for example, radio frequency (RF) waves. Image receiver 10, e.g. an RF receiver, may send the data to a data processor 12 and/or to a storage unit 19. Transmitter 50 may also include control capability, although control capability may be included in a separate component. Transmitter 50 may include any suitable transmitter able to transmit images and/or other data (e.g., control data) to a receiving device. Transmitter 50 may transmit via antenna 51. Other transmission methods may be used.

Typically, device 40 may transmit image information in discrete portions. Each portion may typically correspond to an image or frame or may alternatively correspond to a few lines of image data. Other transmission methods are possible, for example, images may be transmitted in compressed format, and/or may be transmitted in portions that may be smaller than whole image frames. Constant and/or variable capture rates and/or transmission rates may be used. Typically, the image data recorded and transmitted may be digital color image data, although in alternate embodiments other image formats (e.g., black and white image data) may be used. Other data formats may also be used. In one embodiment, imager 35 may capture one image per rotation of inner imaging unit 30. In other embodiments image capture may occur subsequent to a rotational movement. Rotation and image capture may occur periodically one after the other or may be activated by command, e.g. with controller 41. Other suitable rates may be used, and rotation rate need not be tied to image capture rate. Both rotation rate and image capture rate may be variable.

Illumination sources 33 may include, for example, one or more "white LEDS" or any other suitable light source, for illuminating the body lumen. In some embodiments, illumination sources may provide, for example, ultra-violet light, infrared. light, or any other desired light or spectral range. In some embodiments of the present invention, illumination source 33 or a substrate containing an illumination source 33 may be rotatable.

Figure 2:
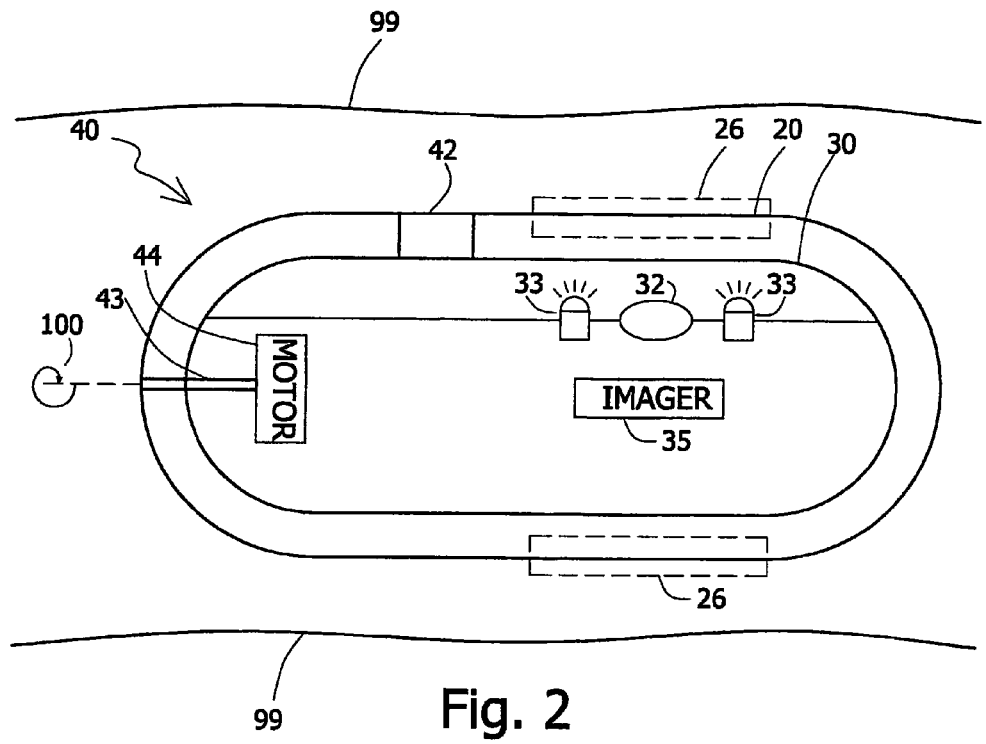
FIG. 2 is a schematic illustration of a sensing device according to another embodiment of the present invention.

In some embodiments of the invention, device 40 and/or imager 35 may have a wide angled field of sensing and/or field of view. In some embodiments, device 40 and/or imager 35 may view and/or capture images of body lumens that may be transverse and/or substantially transverse to the general direction of advancement of device 40 through a body lumen 99 (FIG. 2). In other embodiments, device 40 may sense data other than image data. Furthermore, in some embodiments, device 40 and/or imager 35 may view and/or capture images with a broad field-of-view, e.g., up to 360 degrees. In a further embodiment more than one imager 35 may be incorporated in device 40 and/or imaging unit 30 that may capture images substantially simultaneously, for example, in substantially different directions. In other embodiments of the present invention, data other than image data, e.g. temperature, pH, or other data, may be sensed with a wide field of sensing and/or in one or more fields of sensing.

FIG. 2 depicts an alternative configuration of the imager of device 40 according to some embodiments of the present invention. In FIG. 2 not all the elements are shown for reasons of clarity. Referring to FIG. 2, imager 35, illumination source 33 and optical system 32 may be positioned in alternative configurations within inner imaging unit 30. For example, the field of view of imager 35 and/or the field of illumination of illumination source 33 may be substantially perpendicular to the axis of rotation 100.

According to one embodiment of the present invention, a transparent area 26 may surround shell 20, for example, in a ring shape, so as to enable for example a 360 degree view. According to another embodiment of the present invention, all or portions of inner unit 30 may be transparent to enable suitable illumination and capturing of images.

According to some embodiments the device 40 need not include an imaging unit 30 but rather may include a sensing unit. The sensing unit may include in-vivo sensors, such as, for example, pH sensors, temperature sensors, pressure sensors, electrical impedance sensors, biosensors etc., that may be sensed at alterable fields or with wide fields of sensing. In one embodiment of the present invention, imager 35 may be replaced by a different in-vivo sensor. According to some embodiments more than one sensor may be included in the device 40, e.g., an imager and another in-vivo sensor.

In one embodiment, device 40 may include an in-vivo imager 35 that may capture and transmit images of the GI tract while the capsule may pass through the GI lumen. Other lumens maybe imaged.

Figure 3:
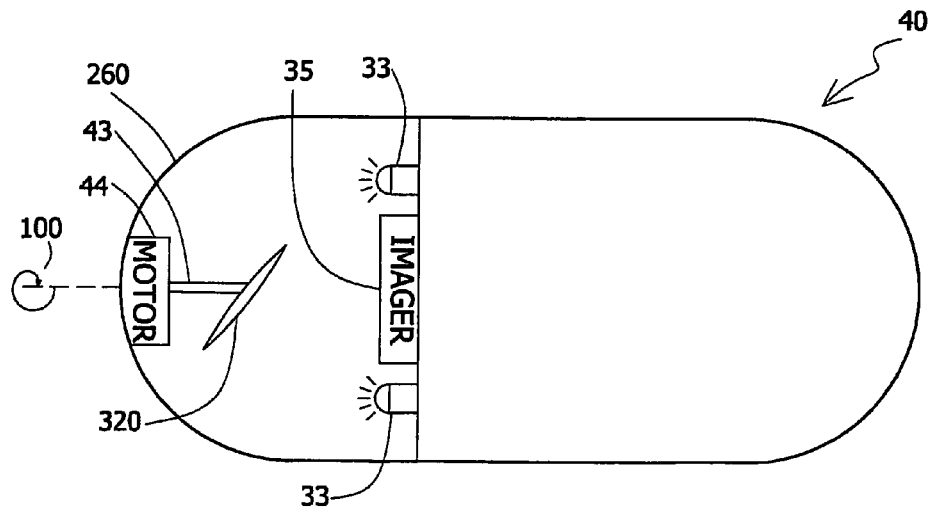
FIG. 3 is a schematic illustration of a sensing device according to yet another embodiment of the present invention.

Another embodiment of the present invention is schematically illustrated in FIG. 3. According to some embodiments, a device 40, which may include elements as described herein, e.g. may include an imager 35 and illumination source(s) 33 for illuminating a body lumen, for example through viewing window 260. According to one embodiment of the present invention, a reflective element 320 may be positioned at a non-90 degree angle, e.g. 30 to 60 degree angle, to imager 35 and may be rotatably engaged or connected to the housing of device 40, e.g. viewing window 260. Motor 44 with shaft or axle 43 may, for example, be engaged to rotate reflective element 320. For example, shaft 43 may be fixed to reflective element 320 and motor 44 may be fixed to, for example, the housing or shell of device 40, e.g. viewing window 260. In other embodiments, the shaft 43 may be fixed to the housing of device 40, e.g. viewing window 260, and the motor 44 may be fixed to the reflective element 320. According to an embodiment of the present invention, motor 44 and shaft 43 may include one or more gear mechanisms, for example, as may be described herein.

According to one embodiment remitted light from in-vivo locations, e.g., a body lumen wall 99 may be incident upon a reflective element 320, e.g. a mirror, and directed (e.g., according to the mirror properties and/or the angle at which the mirror may be positioned) to imager 35. According to some embodiments reflective element 320 may be positioned at an angle with respect to imager 35 and/or with respect to the axis of rotation 100 of the motor 44. Rotation of angled reflective element 320 may, for example, alter the field of view of imager 35. Reflective element 320 may be rotated (for example, by motor 44) with respect to imager 35. Thus, reflective element 320 may direct light onto imager 35 from a field covering for example 360 degrees or may alter the field of view to desired orientations. According to one embodiment illumination source(s) 33 may be arranged in a ring, substantially surrounding the device 40, so as to provide illumination to a 360 degree field. Other suitable fields of view-may be imaged. In some embodiments of the present invention, one or more illumination source(s) 33 may be activated in correspondence to the angle of reflective element 320. In other embodiments of the present invention, illumination source 33 may be rotated together and/or along with reflective element 320. In other embodiments of the present invention, the illumination source may rotated on its own and or may be rotated together with an imager by, for example, mounting illumination source and imager on a common structure. Other suitable methods may be implemented to rotate one or more structures within device 40.

Figure 4:
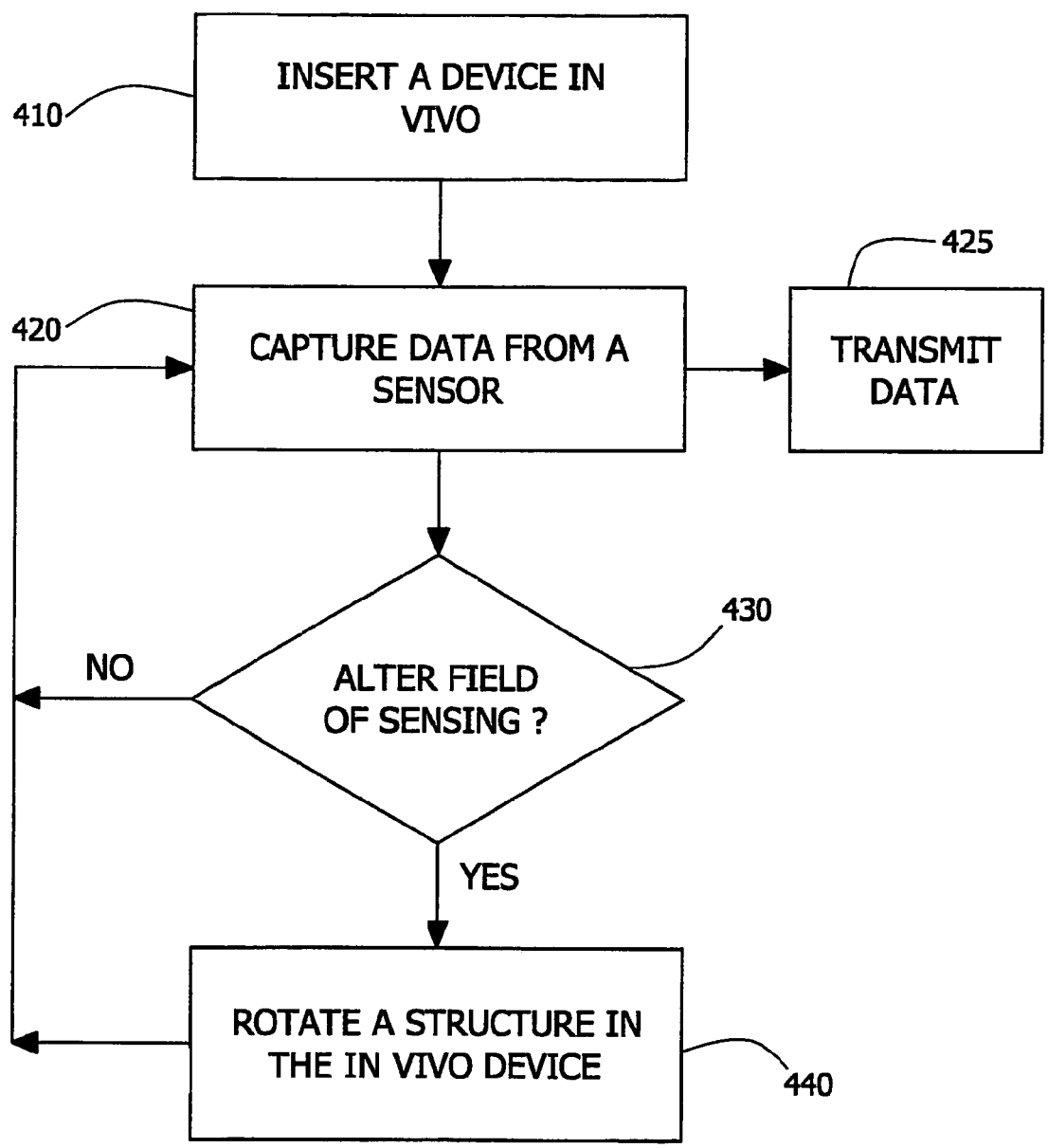
FIG. 4 is a flow chart describing a method for altering a field of view of an in vivo device according to an embodiment of the present invention.

Reference is now made to FIG. 4 showing a flow chart of a method for altering a field of view of an in vivo device according to an embodiment of the present invention. In block 410 an in vivo device, such as device 40 may be inserted in vivo. Insertion may be, for example, by swallowing, inserting with an endoscope, or other suitable methods. In block 420, data may be captured by a sensor, for example, imager 35 or other sensor, for example, temperature sensor, pH sensor, blood detector, location sensor etc. In some embodiments of the present invention, sensed data, e.g. image data may be transmitted (425), for example, to image receiver 10. In other embodiments sensed data may not be transmitted. In block 430 a decision may be made to alter the field of sensing, e.g., field of view of in vivo device 40 based on sensor reading, e.g. pH sensor, image frame capture, etc., or based on other suitable conditions and/or parameters, for example, based on an external command, current field of view of device 40, frame capture rate of imager 35 or other suitable parameters. In some embodiment of the present invention, the decision may be made by controller 41 or other suitable circuitry in device 40. In other embodiments the invention, the decision may be made externally by for example, imager receiver 10 or data processor 12 and, for example, a control command may be transmitted to device 40. Other suitable methods may be implemented. In block 440 a structures of device 40 may be rotated so as to alter the field of view. The rotatable structures may be any structure described herein, e.g. imaging unit 30, mirror 320 or any other suitable structure for altering the field of view or sensing of device 40. In some embodiments of the present invention, rotation may be facilitated by an in-vivo actuator. and/or motor 44 and controlled by controller 41. In other embodiments of the present invention, rotation may be controlled externally, e.g. by a magnetic field, may be facilitated by the influence of gravity or by other suitable methods.

It is noted that while some exemplary embodiments are explained in detail herein, the invention is not limited in this regard, and other embodiments and/or implementations of a broad field-of-view imaging device are also within the scope of the invention. While certain features of the invention have been illustrated and described herein, many modifications, substitutions, changes, and equivalents may occur to those of ordinary skill in the art. The claims are therefore intended to cover all such modifications and changes as fall within the true spirit of the invention.

The invention claimed is:

1. A swallowable in-vivo sensing device comprising:
    a capsule shaped housing having an external shell, said housing enclosing:
        an imaging unit, said imaging unit comprising an imager and an illumination source to capture in vivo images in a field of view; and
        a rotatable structure to alter the field of view of the imaging unit, wherein said rotatable structure rotates said imaging unit relative to and within said external shell of the in-vivo sensing device, wherein the rotatable structure comprises a motor;
    said housing adapted to be swallowed and passed through a patient and containing no physical connection to outside said patient when passing therethrough.

2. The in-vivo sensing device according to claim 1 wherein the imager is a CMOS imager.

3. The in-vivo sensing device according to claim 1, wherein the rotatable structure comprises a gear mechanism.

4. The in-vivo sensing device according to claim 1 comprising a controller to control the rotatable structure.

5. The in-vivo sensing device according to claim 4 wherein the control is in response to an external command.

6. The in-vivo sensing device according to claim 1 comprising a sensor to sense in vivo conditions.

7. The in-vivo sensing device according to claim 1 comprising:
    a transmitter.

8. The in-vivo sensing device according to claim 1 wherein the device is an autonomous capsule.

9. The in-vivo sensing device according to claim 1 having a field of view that is at least partially side viewing.

10. The in-vivo sensing device according to claim 1 wherein said rotatable structure further rotates a transmitter relative to said external shell of the in-vivo sensing device.

11. The in-vivo imaging device according to claim 1 wherein said rotatable structure is fixed to the external shell.

12. The in-vivo sensing device according to claim 1 having a field of view that is substantially side viewing.

13. A system for in-vivo sensing a wide field of view comprising:
    a sensing device, said sensing device comprising a capsule shaped housing having an external shell, said housing enclosing:
        an imaging unit to capture in vivo images in a field of view, said imaging unit comprising an imager and an illumination unit; and
        a rotating means to rotate said imaging unit relative to and within said external shell so as to alter the field of view, wherein the rotating means comprises a motor;
        said housing adapted to be swallowed and passed through a patient and containing no physical connection to outside said patient when passing therethrough:
    a controlling means to control the rotating means; and
    a receiving means for receiving image data.

14. The system according to claim 13 wherein the controlling means is integral to the rotating means.

15. The system according to claim 13 wherein the receiving means is a RF receiver.

16. The system according to claim 13 comprising transmitting means for transmitting commands to the rotating means.

17. The system according to claim 13 comprising a storage means for storing image data.

18. The system according to claim 13 comprising a display means for displaying image data.

19. The system according to claim 13 wherein said sensing device has a field of view that is at least partially side viewing.

20. The system according to claim 13 wherein said sensing device has a field of view that is substantially side viewing.

21. The system according to claim 13 wherein the controlling means generate automatic commands based on data captured by the imaging unit.

* * * * *

UNITED STATES PATENT AND TRADEMARK OFFICE
CERTIFICATE OF CORRECTION

PATENT NO. : 7,625,338 B2
APPLICATION NO. : 11/023524
DATED : December 1, 2009
INVENTOR(S) : Gilad et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 945 days.

Signed and Sealed this

Twenty-sixth Day of October, 2010

David J. Kappos
*Director of the United States Patent and Trademark Office*